US012636044B2

(12) United States Patent
Schwamb et al.

(10) Patent No.: US 12,636,044 B2
(45) Date of Patent: May 26, 2026

(54) MOUNT FOR HOLDING REFERENCE FRAME DURING A SURGICAL PROCEDURE

(71) Applicant: Medtronic Navigation, Inc., Louisville, CO (US)

(72) Inventors: Jeffrey M. Schwamb, Broomfield, CO (US); Kristen Temnyk, Wheat Ridge, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 327 days.

(21) Appl. No.: 18/299,835

(22) Filed: Apr. 13, 2023

(65) Prior Publication Data

US 2023/0363796 A1      Nov. 16, 2023

Related U.S. Application Data

(60) Provisional application No. 63/342,325, filed on May 16, 2022.

(51) Int. Cl.
A61B 17/70      (2006.01)
A61B 17/84      (2006.01)

(52) U.S. Cl.
CPC .............. A61B 17/70 (2013.01); A61B 17/84 (2013.01)

(58) Field of Classification Search
CPC . A61B 17/70; A61B 17/7002; A61B 17/7007; A61B 17/7032; A61B 17/7034; A61B 17/7076; A61B 34/20; A61B 2090/3983; A61B 2034/2055
USPC ......................................................... 606/60
See application file for complete search history.

(56) References Cited

U.S. PATENT DOCUMENTS

| | | | |
|---|---|---|---|
| 3,783,547 | A | 1/1974 | Bystrom et al. |
| 3,904,200 | A | 9/1975 | Jackle et al. |
| 7,787,934 | B2 | 8/2010 | Mazzocchi et al. |
| 8,057,407 | B2 | 11/2011 | Martinelli et al. |
| 8,185,184 | B2 | 5/2012 | Solar et al. |
| 9,737,235 | B2 | 8/2017 | Hartmann |
| 10,531,814 | B2 | 1/2020 | Reddy et al. |
| 10,835,296 | B2 | 11/2020 | Elimelech et al. |
| 11,135,015 | B2 | 10/2021 | Crawford et al. |
| 11,786,324 | B2 * | 10/2023 | Crawford ........... A61B 17/7001 600/424 |
| 11,911,079 | B2 * | 2/2024 | Braal ....................... A61F 2/447 |
| 2004/0019263 | A1 | 1/2004 | Jutras et al. |
| 2006/0100508 | A1 | 5/2006 | Morrison |

(Continued)

OTHER PUBLICATIONS

International Search Report and Written Opinion of related International Application No. PCT/IB2023/054974; dated: Jul. 28, 2023; 16 pages.

*Primary Examiner* — Eduardo C Robert
*Assistant Examiner* — Christina Negrellirodriguez
(74) *Attorney, Agent, or Firm* — Mueting Raasch Group

(57)      ABSTRACT

A mount for holding a reference frame during a surgical procedure. The mount includes a reference frame connector at a first end of the mount. A shank connector is at a second end of the mount. The shank connector is configured to receive a head of a shank within the shank connector. The shank connector includes a set screw movable to contact the head to lock the shank connector to the head of the shank. A support rod extends between the reference frame connector and the shank connector.

16 Claims, 6 Drawing Sheets

(56)          References Cited

U.S. PATENT DOCUMENTS

| | | | |
|---|---|---|---|
| 2011/0118750 A1* | 5/2011 | Wu | A61B 34/20 |
| | | | 606/130 |
| 2019/0209154 A1* | 7/2019 | Richter | A61B 1/32 |
| 2019/0216560 A1 | 7/2019 | Bono et al. | |
| 2019/0269469 A1 | 9/2019 | Bush, Jr. et al. | |
| 2020/0360091 A1* | 11/2020 | Murray | A61B 90/39 |

* cited by examiner

MOUNT FOR HOLDING REFERENCE FRAME DURING A SURGICAL PROCEDURE

CROSS-REFERENCE TO RELATED APPLICATIONS

This application claims the benefit of U.S. Provisional Application No. 63/342,325 filed on May 16, 2022. The entire disclosure of the above application is incorporated herein by reference.

FIELD

The present disclosure relates to a mount for holding a reference frame during a surgical procedure.

BACKGROUND

This section provides background information related to the present disclosure, which is not necessarily prior art.

When working with a pediatric patient afflicted with a deformity, such as scoliosis, it is often the case where a pedicle of a vertebral body is small, nonexistent, or of poor bone quality. Such patients are usually treated using surgical navigation technology, which relies on placement of a reference frame in the surgical field by mounting the reference frame to a pedicle with a clamp. If a surgeon is unable to use a spine clamp due to insufficient bone structure, the reference frame must be attached in a different manner. The present disclosure advantageously includes a mount for holding a reference frame during surgery, which addresses various needs in the art as explained herein and as one skilled in the art will appreciate.

SUMMARY

This section provides a general summary of the disclosure, and is not a comprehensive disclosure of its full scope or all of its features.

The present disclosure provides for a mount for holding a reference frame during a surgical procedure. The mount includes a reference frame connector at a first end of the mount. A shank connector is at a second end of the mount. The shank connector is configured to receive a head of a shank within the shank connector. The shank connector includes a set screw movable to contact the head to lock the shank connector to the head of the shank. A support rod extends between the reference frame connector and the shank connector.

The present disclosure further provides for a mount for holding a reference frame during a surgical procedure. The mount includes a reference frame connector at a first end of the mount. A shank connector is at a second end of the mount. The shank connector has a main body defining a receptacle, a distal opening, and a side window adjacent to the distal opening configured to receive a head of a shank. A support rod extends between the reference frame connector and the shank connector.

The present disclosure also provides for a method for performing a navigated surgical procedure. The method includes the following: securing a shank to a bone; connecting a mount holding a reference frame to the shank by sliding a shank connector of the mount onto a head of the shank so that the head passes through a side window defined by a main body of the shank connector into a receptacle defined by the main body; tightening a set screw of the shank connector so that the set screw contacts the head of the shank to apply pressure to the head and secure the head within the receptacle; using the reference frame during the navigated surgical procedure; detaching the mount from the shank after use of the reference frame has concluded; and attaching a bracket to the shank after the mount has been detached from the shank, the bracket configured to couple with an implant.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 6 is a perspective view of an exemplary shank, which the shank connector of the mount of FIG. 1 is configured to cooperate with;

FIG. 7 is a perspective view of the shank in cooperation with bone, and of the shank connector of the mount in cooperation with a head of the shank;

Corresponding reference numerals indicate corresponding parts throughout the several views of the drawings.

DETAILED DESCRIPTION

Example embodiments will now be described more fully with reference to the accompanying drawings.

Figures 1, 2:
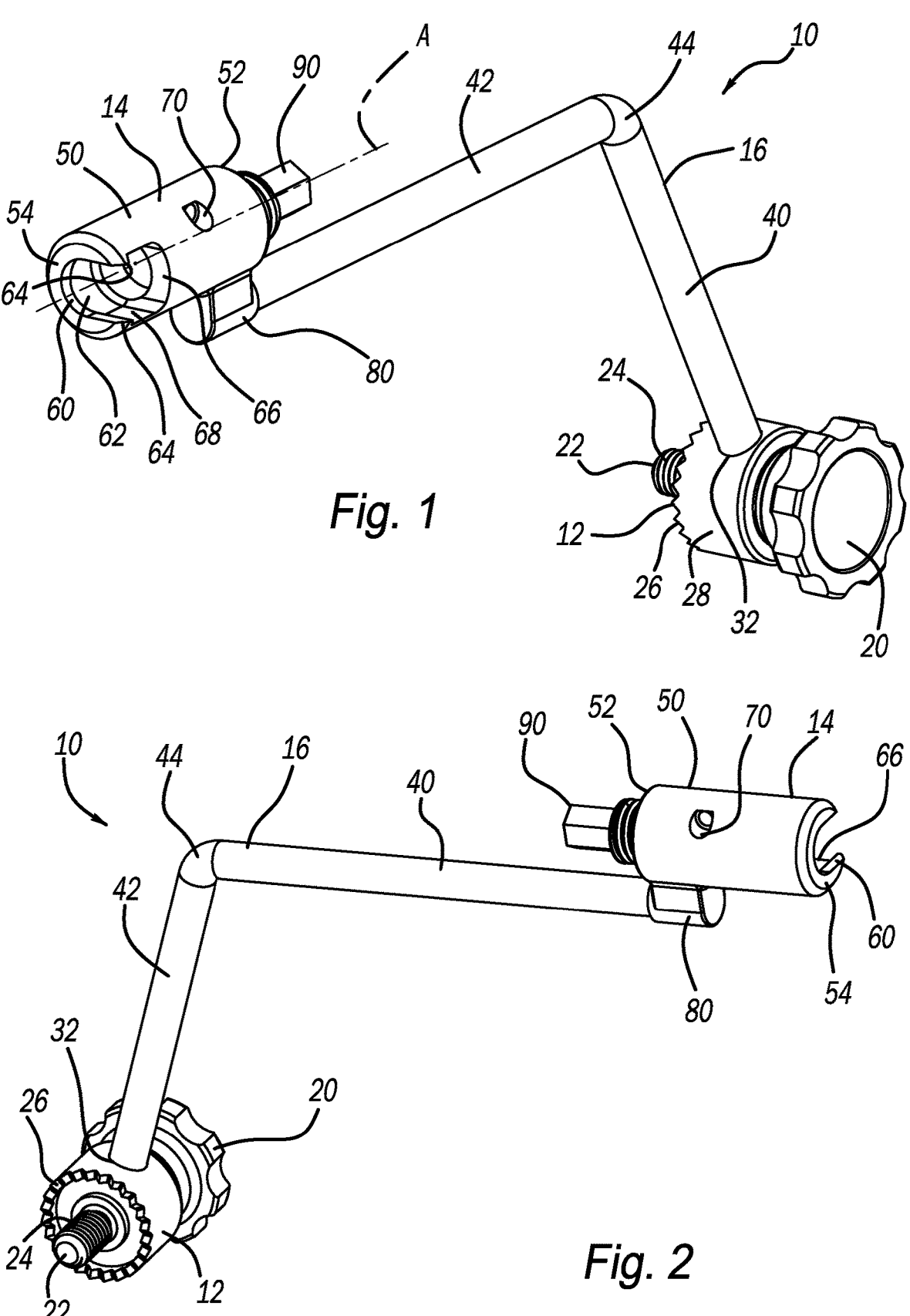
FIG. 1 is a perspective view of a mount in accordance with the present disclosure for holding a reference frame during a surgical procedure.
FIG. 2 is another perspective view of the mount of FIG. 1.
Figure 3:
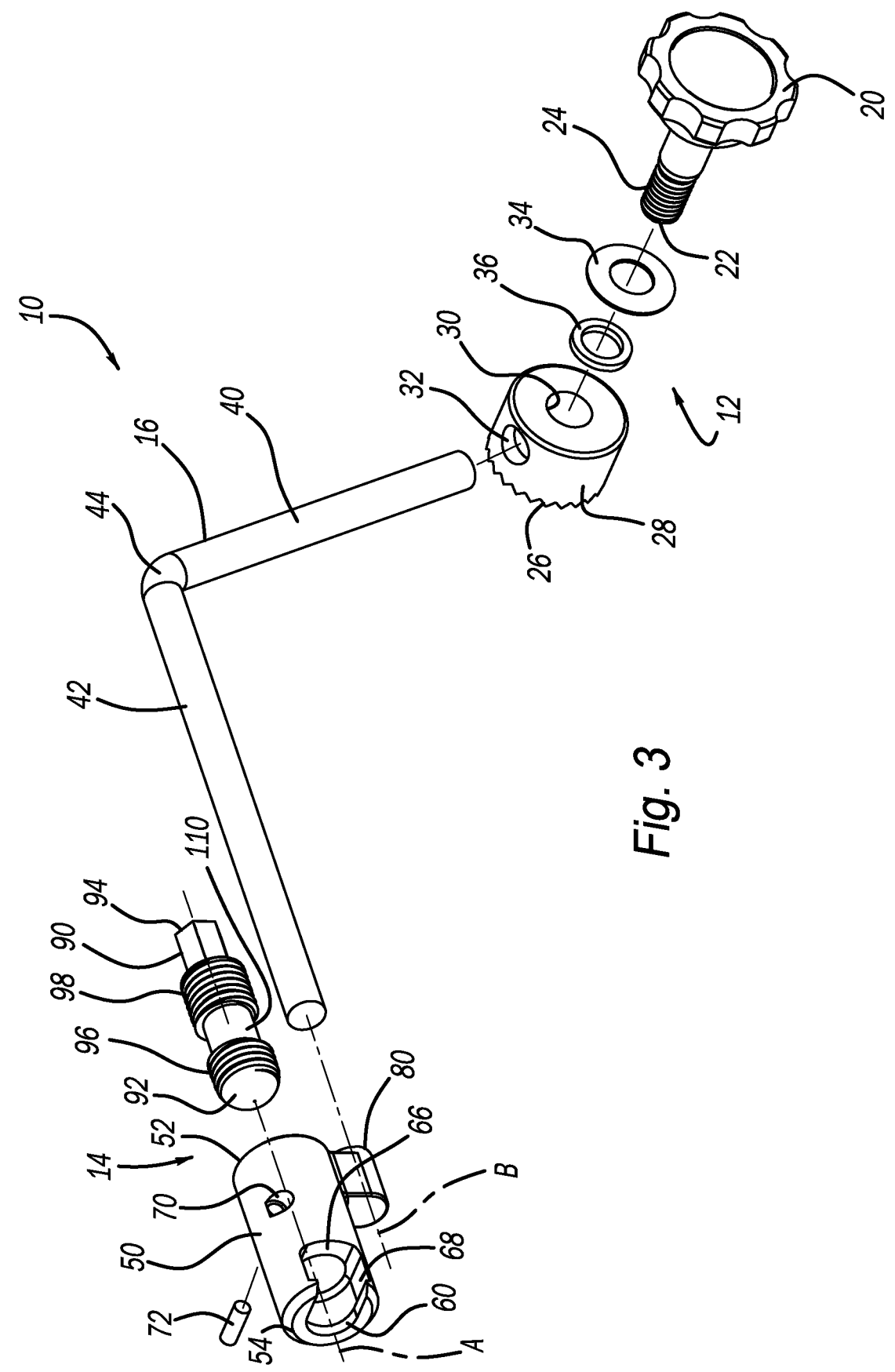
FIG. 3 is an exploded view of the mount of FIG. 1.
Figure 8:
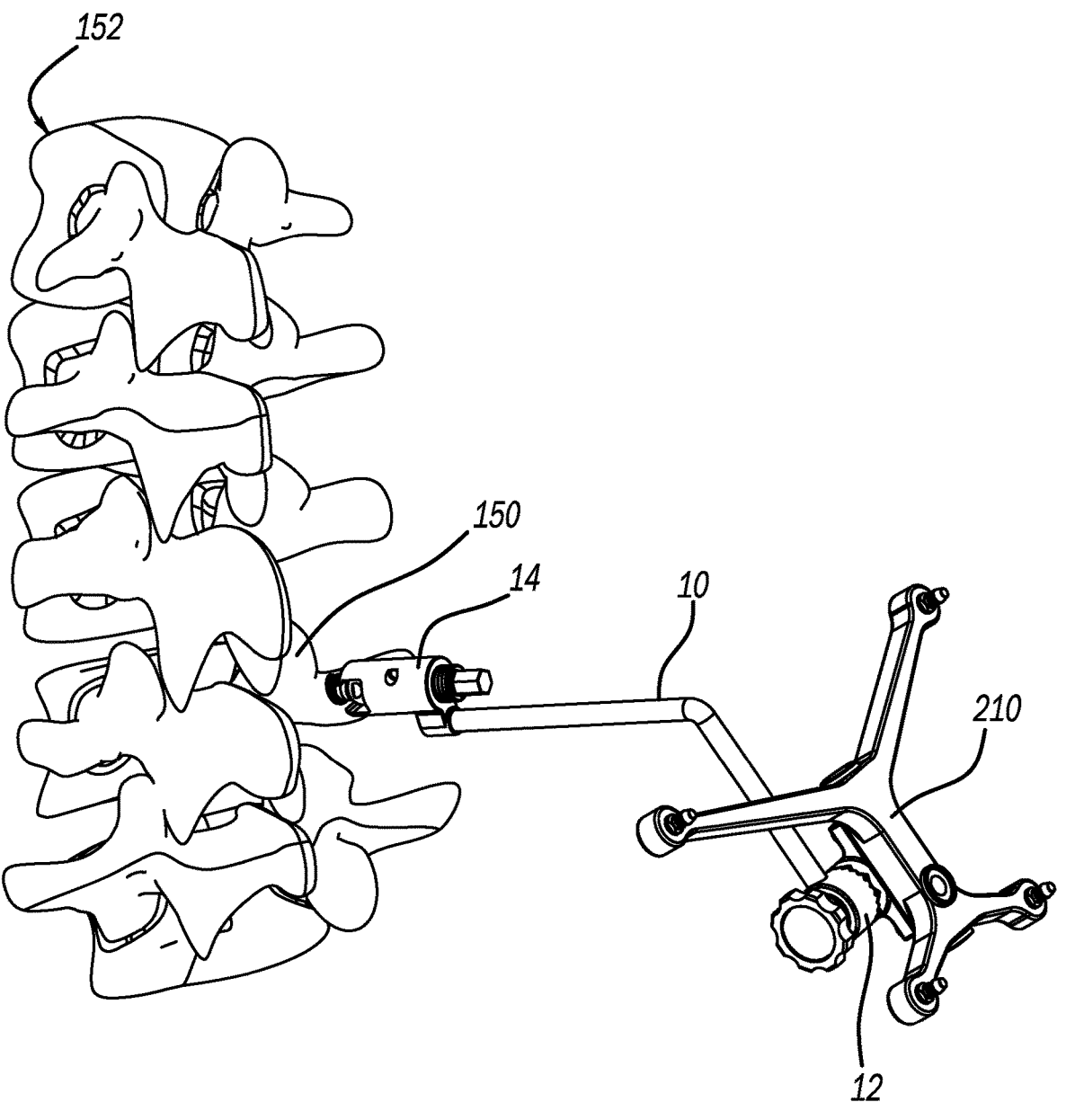
FIG. 8 is a perspective view of the mount with the reference frame mounted thereto, the mount is connected to a shank that is in cooperation with bone of a spine.

With the initial reference to FIGS. 1-3, a mount 10 in accordance with the present disclosure is illustrated. The mount 10 is configured to mount any suitable reference frame relative to an anatomy during a surgery that uses surgical navigation technology. FIG. 8 illustrates an exemplary reference frame 210. The mount 10 may be used to mount any other suitable reference frame or other tracking device as well. For example, the mount 10 may be used with any of the surgical navigation devices and systems described in the following references, each of which is incorporated herein by reference in its entirety: U.S. Pat. Nos. RE44,305; 7,697,972; 8,644,907; and 8,842,893; and U.S. Pat. App. Pub. Nos. 2004/0199072.

The mount 10 generally includes a reference frame connector 12, a shank connector 14, and a support rod 16 extending between the reference frame connector 12 and the shank connector 14. The support rod 16 may have any suitable shape to support the reference frame 210 at a desired position relative to the shank connector 14 and the anatomy that the mount 10 is mounted to.

The reference frame connector 12 may have any suitable configuration for connecting the mount 10 to the reference frame 210, or any other suitable reference frame or tracking device. In the example illustrated, the reference frame connector 12 includes a knob 20 with a shaft 22 extending therefrom. The shaft 22 includes a plurality of threads 24, which are configured to cooperate with threads of the reference frame 210 or an associated bracket. A plurality of teeth 26 are configured to cooperate with corresponding teeth of the reference frame 210 (or an associated bracket) to allow the reference frame 210 to be supported at a variety of different rotational positions relative to the reference frame connector 12. With particular reference to FIG. 3, the reference frame connector 12 includes a housing 28, which defines a first aperture 30 and a second aperture 32. The shaft 22 extends through the first aperture 30 such that the knob 20 and the threads 24 are on opposite sides of the housing 28. Seated on the shaft 22 is a first washer 34 and a second washer 36. The support rod 16 is secured within the second aperture 32. Alternatively, the support rod 16 and the housing 28 may be integral, such as in the form of a unitary, monolithic structure.

In the example illustrated, the support rod 16 includes a first portion 40, a second portion 42, and an elbow 44, which is between the first portion 40 and the second portion 42. The first portion 40 extends from the housing 28 of the reference frame connector 12. The second portion 42 extends from the shank connector 14, as described in further detail herein. The elbow 44 may be curved or angled to arrange the first portion 40 and the second portion 42 at any suitable angles relative to one another. The elbow 44 is optional, and thus in some applications the support rod 16 may be linear.

With continued reference to FIGS. 1-3, and additional reference to FIG. 4, the shank connector 14 will now be described in additional detail. The shank connector 14 includes a main body 50 having a proximal end 52 and a distal end 54, which is opposite to the proximal end 52. A longitudinal axis A extends through the main body 50 and through a center of the proximal end 52 and a center of the distal end 54.

At the distal end 54 is a distal opening 60. The distal opening 60 provides access to a receptacle 62 defined by the main body 50. The distal opening 60 is defined by a flange 64, which is generally c-shaped and extends around less than an entirety of the distal opening 60. The main body 50 also defines a window 66, which is at a side of the main body 50 adjacent to the flange 64 and the distal opening 60. The window 66 provides access to the receptacle 62 from a direction that is perpendicular to the longitudinal axis A. At the window 66 is a recess 68, which is adjacent to the flange 64.

The main body 50 further defines a pinhole 70. The pinhole 70 extends perpendicular to, and is offset from, the longitudinal axis A of the main body 50. The pinhole 70 is configured to receive a pin 72 (see FIG. 3) for retaining a set screw 90 within the main body 50, as further described herein.

Adjacent to the main body 50 is a side body 80 of the shank connector 14. The side body 80 extends along a longitudinal axis B, which is parallel to the longitudinal axis A of the main body 50. The side body 80 cooperates with the support rod 16 in any suitable manner. For example, the side body 80 may define a receptacle in receipt of the second portion 42 of the support rod 16. Alternatively, the second portion 42 may be integral with, and monolithic with, the side body 80.

The set screw 90 includes a head 92 and a base end 94, which is opposite to the head 92. Distal threads 96 are adjacent to the head 92, and proximal threads 98 are adjacent to the base end 94. Between the distal threads 96 and the proximal threads 98 is an outer surface 110, which is without threads. The set screw 90 is retained within the main body 50 by the pin 72, which sits against the outer surface 110 between the distal threads 96 and the proximal threads 98 when the set screw 90 is seated within the main body 50. The set screw 90 may be screwed into the main body 50 until the pin 72 contacts the proximal threads 98, and the set screw 90 may be rotated in an opposite direction to move the head 92 away from the distal end 54 until the pin contacts the distal threads 96.

The distal threads 96 and the proximal threads 98 cooperate with internal threads of the main body 50. Thus, rotation of the set screw 90 in a first direction moves the set screw 90 along the longitudinal axis A towards the distal end 54 of the main body 50. Rotation of the set screw 90 in an opposite direction moves the set screw 90 along the longitudinal axis A towards the proximal end 52 of the main body 50. The base end 94 may include a plurality of flat surfaces to facilitate cooperation between the base end 94 and any suitable tool for rotating the set screw 90. Planar surfaces may also facilitate manual rotation of the set screw 90.

Figures 4, 5:
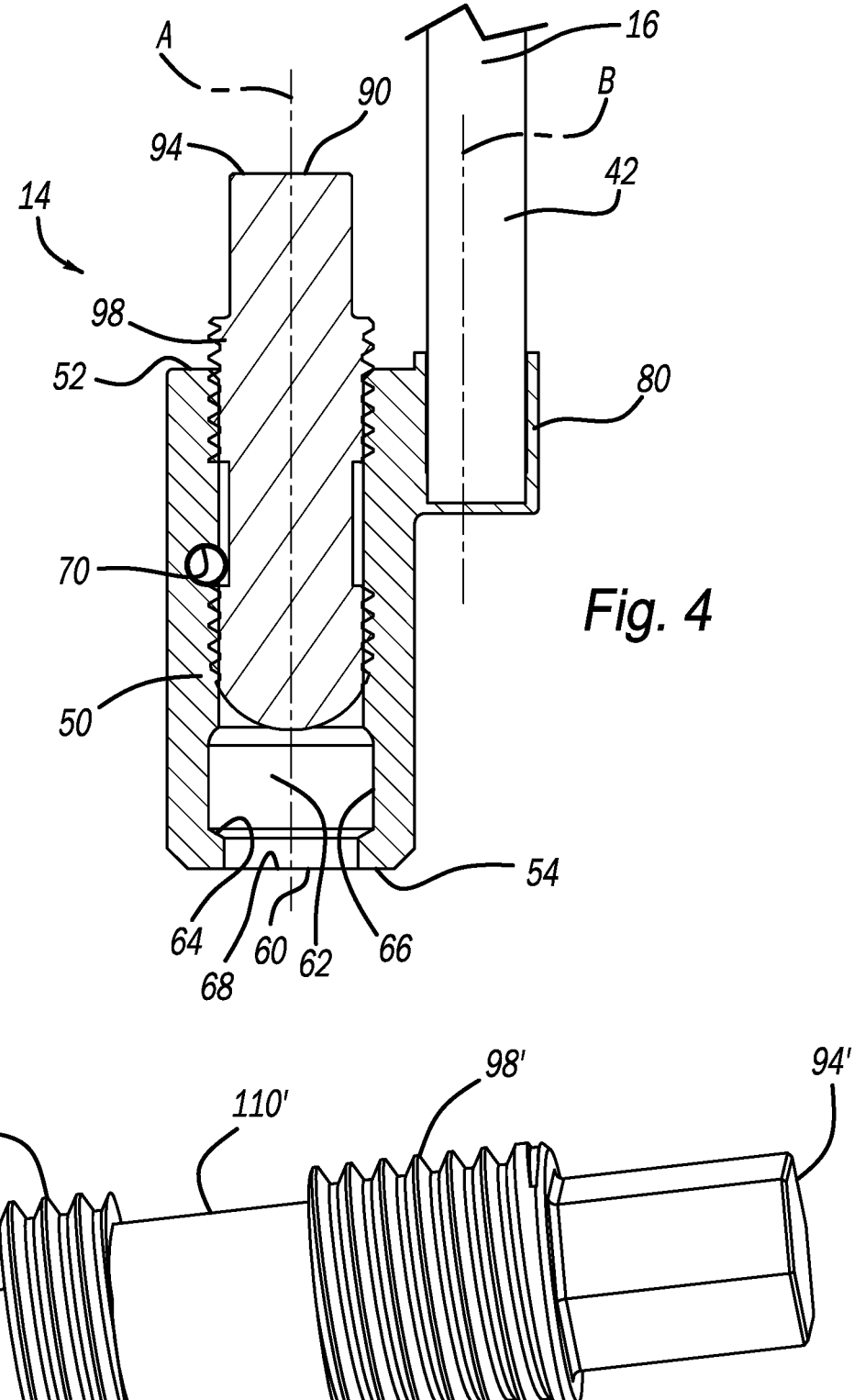
FIG. 4 is a cross-sectional view of a shank connector of the mount of FIG. 1.
FIG. 5 is a perspective view of an alternate set screw for cooperation with the shank connector of the mount of FIG. 1.

FIG. 5 illustrates an additional set screw in accordance with the present disclosure at reference numeral 90'. The set screw 90' is similar to the set screw 90, and thus like features are identified in FIG. 5 using the same reference numerals, but further including the prime symbol ('). The description of the set screw 90 also applies to the set screw 90', except that the head 92' is flat, which is in contrast to the round head 92.

Figures 6, 7:
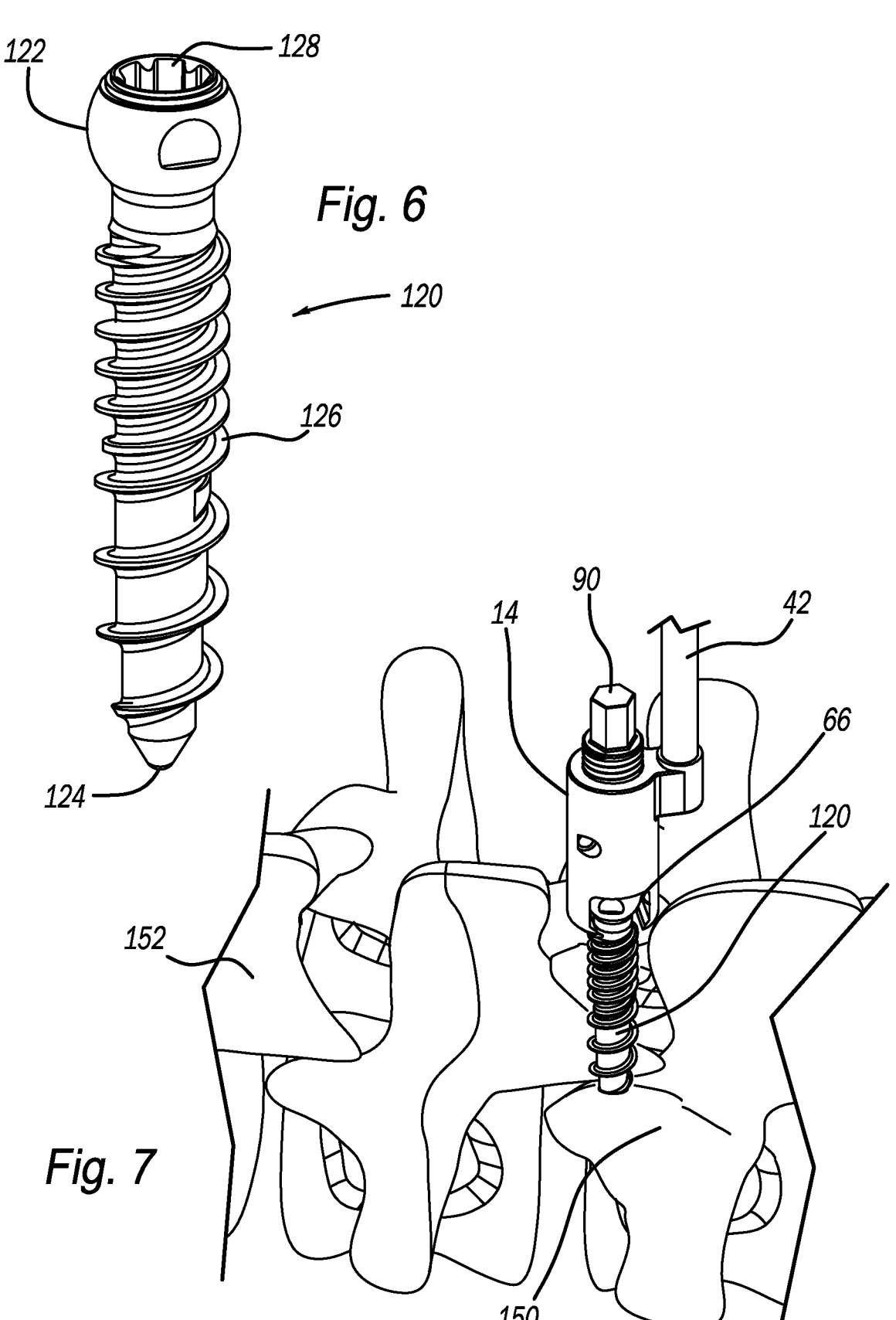

FIG. 6 illustrates an exemplary shank (or screw) 120 configured to cooperate with the shank connector 14. The shank 120 may be any shank, screw, or fastener suitable for attaching to bone. In the example illustrated, the shank 120 includes a head 122 and a tip 124. Between the head 122 and the tip 124 are a plurality of threads 126. The head 122 defines a receptacle 128 for cooperating with a fastener, as explained further herein. The head 122 is configured in any suitable manner to cooperate with the main body 50 of the shank connector 14.

FIG. 7 illustrates the shank 120 screwed into bone 150. The bone 150 may be any suitable bone of a patient, such as a vertebral body of a spine 152. The mount 10 is connected to the shank 120 by coupling the shank connector 14 to the head 122 of the shank 120. Specifically, after the shank 120 is secured to the bone 150, the main body 50 of the shank connector 14 is slid over the head 122 in a direction perpendicular to the longitudinal axis A of the main body 50 so the head 122 enters the receptacle 62 through the side window 66. The window 66 allows the main body 50 to be slid laterally onto the head 122 of the shank 120, which advantageously gives the surgeon more room to work along the midline of the spine 152. The flange 64 is seated on an underside of the head 122 to restrict movement of the main body 50 vertically off of the head 122. With the head 122 seated in the receptacle 62, the set screw 90/90' is rotated and tightened to move the head 92 (or the head 92' when the set screw 90' is used) into cooperation with the head 122 of the shank 120, which further strengthens the cooperation between the shank connector 14 and the shank 120.

FIG. 8 illustrates the mount 10 used to support the reference frame 210 during a spinal procedure. The mount 10 is connected to the shank 120, which has been inserted into bone 150 (such as a vertebral body) of the spine 152. The mount 10 may be oriented in any suitable position to optimally arrange the reference frame 210 for a navigated procedure.

Figures 9, 10:
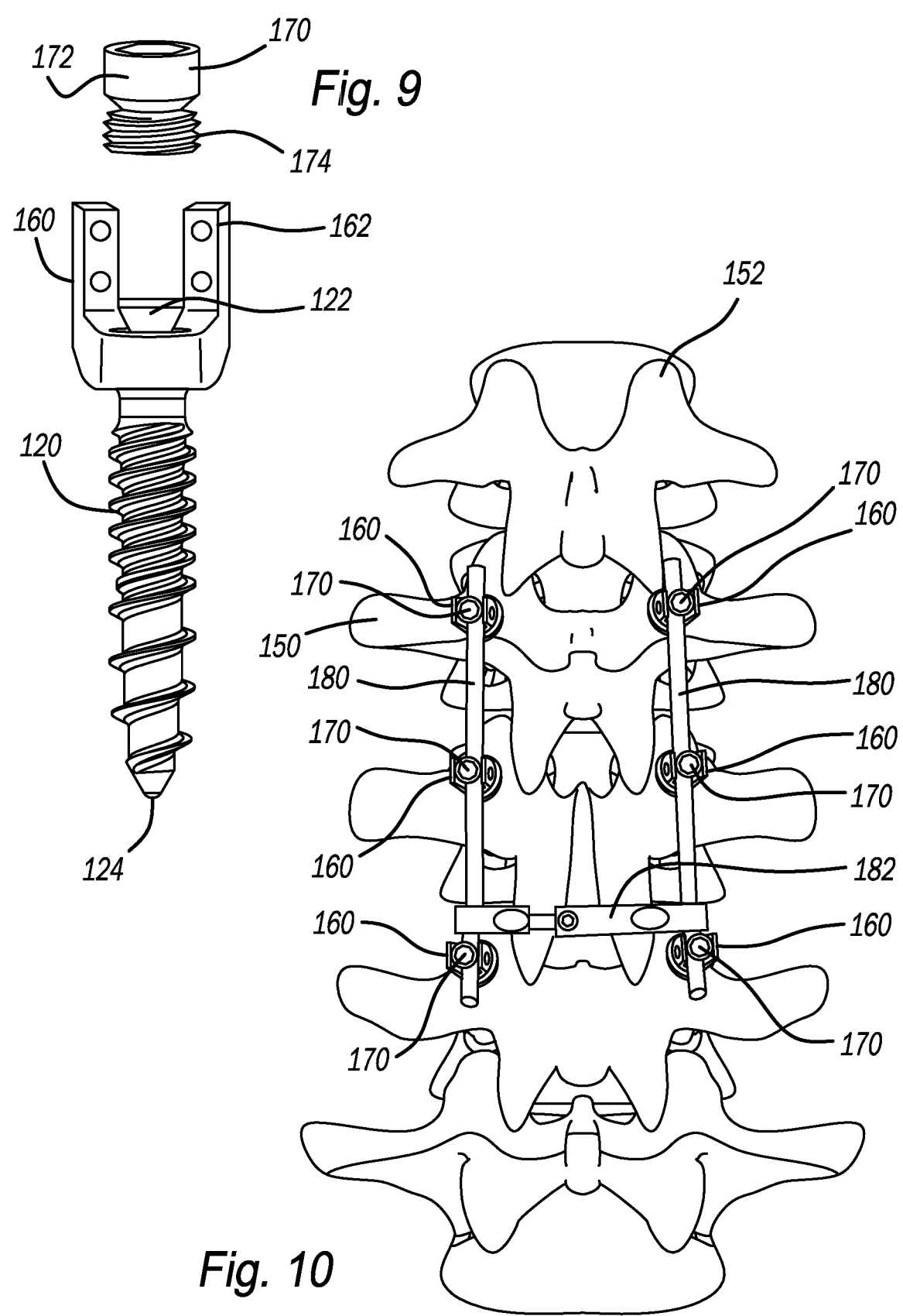
FIG. 9 illustrates the shank with a bracket seated thereon, and a fastener configured to cooperate with the bracket.
FIG. 10 is a plan view of a spine, a pair of support rods and a cross-connector are mounted over the spine with a plurality of the shanks and brackets.

Once the reference frame 210 is no longer needed, the mount 10 is disconnected from the shank 120. With additional reference to FIGS. 9 and 10, a bracket 160, such as a tulip head bracket, is connected to the head 122 of the shank 120 by sliding the bracket 160 laterally onto the head 122. FIG. 10 illustrates a plurality of shanks 120 secured to different bones of the spine 152. Each one of the shanks 120 has a tulip head bracket 160 connected thereto. The tulip head brackets 160 are configured to receive alignment/reinforcement rods 180 within U-shape portions 162 thereof. The rods 180 are secured in place by screwing a fastener 170 onto the rods 180. The fastener 170 includes a head 172 and threads 174. The threads 174 are configured to cooperate with internal threads of the tulip head bracket 160 to lock the rods 180 in place. As illustrated in FIG. 10, a connector 182 may be coupled to, and extend between, adjacent rods 180 to further strengthen the assembly.

The mount 10 is suitable for use in any relevant surgical procedure, such as, but not limited to, pediatric patients afflicted with scoliosis or other spinal issues. The mount 10 is particularly configured for use with patients whose sinus process is degraded or missing. The mount 10 is equally suitable for use in initial procedures or revision surgical procedures.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A mount for holding a reference frame during a surgical procedure, the mount comprising:

a reference frame connector at a first end of the mount;

a shank connector at a second end of the mount, the shank connector is configured to receive a head of a shank within the shank connector, the shank further comprising a tip configured to be secured to a bone, the shank connector including a set screw configured to be screwed into a main body of the shank connector and movable to contact the head to lock the shank connector to the head of the shank, wherein the main body of the shank connector comprises a proximal end and a distal end, at the distal end the main body defines a distal opening, the set screw extends through the proximal end into the main body, wherein the main body further defines a side window adjacent to the distal end, at the side window is a recess that is adjacent to a flange at the distal end, and further wherein the side window is configured to receive the head of the shank by sliding the main body over the head in a direction perpendicular to a longitudinal axis extending through the main body; and a support rod extending between the reference frame connector and the shank connector.

2. The mount of claim 1, wherein the reference frame connector includes a knob, a threaded shaft extending from the knob, and a plurality of teeth extending about the threaded shaft.

3. The mount of claim 1, wherein the support rod includes a first portion extending from the reference frame connector, a second portion extending from the shank connector, and an elbow portion between the first portion and the second portion.

4. The mount of claim 3, wherein the first portion is angled relative to the second portion.

5. The mount of claim 1, wherein the set screw extends along a longitudinal axis of the main body of the shank connector.

6. The mount of claim 5, wherein the longitudinal axis extends parallel to a portion of the support rod connected to the shank connector.

7. The mount of claim 1, wherein the set screw includes a rounded head.

8. The mount of claim 1, wherein the set screw includes a flat head.

9. The mount of claim 1, wherein the main body defines a pin hole extending perpendicular to, and offset from, a longitudinal axis of the main body, the pin hole is configured to receive a pin, the pin hole is positioned to direct the pin into cooperation with the set screw to retain the set screw within the main body.

10. A mount for holding a reference frame during a surgical procedure, the mount comprising:

a reference frame connector at a first end of the mount;

a shank connector at a second end of the mount, the shank connector including a main body defining a receptacle, a distal opening, and a side window adjacent to the distal opening configured to receive a head of a shank, wherein the side window is configured to receive the head of the shank by sliding the main body over the head in a direction perpendicular to a longitudinal axis extending through the main body, and further wherein the shank further comprises a tip configured to be secured to a bone; and a support rod extending between the reference frame connector and the shank connector.

11. The mount of claim 10, further comprising a set screw seated in the main body, the set screw movable along a longitudinal axis of the main body to contact the head of the shank to lock the head within the receptacle of the shank connector.

12. The mount of claim 11, wherein the main body includes a proximal end and a distal end at the distal opening, the longitudinal axis of the main body extends between the proximal end and the distal end through a radial center of the set screw.

13. The mount of claim 12, where at least a portion of the support rod extends parallel to the longitudinal axis.

14. A method for performing a navigated surgical procedure comprising;

securing a shank to a bone;

connecting a mount holding a reference frame to the shank by sliding a shank connector of the mount onto a head of the shank so that the head passes through a side window defined by a main body of the shank connector into a receptacle defined by the main body;

tightening a set screw of the shank connector so that the set screw contacts the head of the shank to apply pressure to the head and secure the head within the receptacle;

using the reference frame during the navigated surgical procedure;

detaching the mount from the shank after use of the reference frame has concluded; and attaching a bracket to the shank after the mount has been detached from the shank, the bracket configured to couple with an implant.

15. The method of claim 14, further comprising securing the implant to the bracket, wherein the implant is a spinal rod.

16. The method of claim 14, wherein detaching the mount from the shank includes untightening the set screw from the head of the shank.

* * * * *